United States Patent
Tikhonov et al.

(10) Patent No.: US 8,003,142 B2
(45) Date of Patent: Aug. 23, 2011

(54) THERAPEUTIC AND COSMETIC BALSAM

(75) Inventors: Vladimir Petrovich Tikhonov, Moscow (RU); Valery Gennadievich Makarov, St. Petersburg (RU); Lyudmila Konstantinovna Gavrovskaya, St. Petersburg (RU); Dmitry Pavlovich Sidlyarov, Moscow (RU)

(73) Assignee: Otkrytoe Aktsionernoe Obschestvo Zavod Ekologischeeskoy Tekhniki I Ekopitaniya "DIOD", Moscow (RU)

( * ) Notice: Subject to any disclaimer, the term of this patent is extended or adjusted under 35 U.S.C. 154(b) by 278 days.

(21) Appl. No.: 12/158,488

(22) PCT Filed: Jan. 18, 2006

(86) PCT No.: PCT/RU2006/000011
§ 371 (c)(1),
(2), (4) Date: Nov. 10, 2008

(87) PCT Pub. No.: WO2007/073232
PCT Pub. Date: Jun. 28, 2007

(65) Prior Publication Data
US 2009/0081321 A1 Mar. 26, 2009

(30) Foreign Application Priority Data

Dec. 23, 2005 (RU) ................................ 2005140191

(51) Int. Cl.
*A61K 36/81* (2006.01)
*A61K 36/899* (2006.01)
(52) U.S. Cl. ........................................ 424/760; 424/750
(58) Field of Classification Search ........................ None
See application file for complete search history.

(56) References Cited

U.S. PATENT DOCUMENTS

| 6,667,047 B2 | 12/2003 | Brown et al. |
| 6,759,056 B2 * | 7/2004 | Jordan .......................... 424/449 |
| 6,946,144 B1 | 9/2005 | Jordan |

FOREIGN PATENT DOCUMENTS

| RU | 1794454 A1 | 2/1993 |
| RU | 2127584 C1 | 3/1999 |
| RU | 2193394 C1 | 11/2002 |
| RU | 2229285 C1 | 5/2004 |
| RU | 2234935 C1 | 8/2004 |
| WO | 00/62751 A2 | 10/2000 |

OTHER PUBLICATIONS

Staya "Iz chego sostoyat kosmeticheski kremy", [on-line], statya dobavlena Oct. 27, 2004, [found on Aug. 22, 2006], Found on Internet: http://www.famiilyshop.ru/articles/article_info/29, 7 pages.
International application No. PCT/RU2006/000011: Search Report dated Aug. 31, 2006, 1 page.

* cited by examiner

*Primary Examiner* — Christopher R Tate
*Assistant Examiner* — Melenie McCormick
(74) *Attorney, Agent, or Firm* — Gail C. Silver; Borden Ladner Gervais LLP

(57) ABSTRACT

The invention relates to cosmetics and medicine and can be used for skin care or in form of a warming balsam. The present oily balsam represents a homogenous system and comprises a complex of the following oils, emollients and extracts: Macadamia oil, Bosvellia serrata extract (olibanum), isopropyl myristate, vegetable oil, oil extract of red hot pepper standardized for capsaicin (10%), polyethylsiloxane (PES-4), lecithin and a flavouring agent at a certain ratio of the components. The balsam has a more pronounced prolonged warming, anaesthetic, anti-inflammatory and regeneration action and has pleasant organoleptic properties and texture.

3 Claims, No Drawings

THERAPEUTIC AND COSMETIC BALSAM

FIELD OF INVENTION

The invention relates to the field of cosmetics and medicine and can be used for skin care and as a warming balsam.

PRIOR ART

During the lifetime certain chemical alterations take place in an organism that act on the skin. Such alterations are caused by various factors: sun abuse, temperature differences, low humidity, a polluted atmosphere, stress, malnutrition, alcohol, smoking, sleeplessness, physical stress or infectious diseases. Many of these factors lead to early aging and withering of the skin.

All this is taken into account by practical therapeutic cosmetology, and makes research on new low-toxic preparations of combined effect, possessing anti-inflammatory, rejuvenating and other useful properties, a problem of current concern. Preparations of natural origin meet these requirements best.

Known is a transdermal system for application of cosmetic and pharmaceutical agents to the skin for pain relief or reducing inflammations. The system comprises ethoxylated lipids, an alcohol as penetration enhancer, and an aqueous adjuvant with aloe. The system is used for application of a substances of the group including capsaicin, Boswellin, NSAID, and collagen. Boswellin is produced from known commercial extracts. An increased effect can be observed that is due to achieving a higher dose of active substance, i.e., a better penetration through the skin (U.S. Pat. No. 6,946,144 A, Sep. 20, 2005, A61K9/70, ORYXE (CA), Transdermal delivery system). Despite the efficacy of the known composition its field of application is limited basically to rheumatic diseases as it has an irritant action.

Known is also a balsamic ointment "Karagaj" containing an oily extract of hot pepper, an alcoholic solution of resin from the Schrenk spruce, camphor, menthol, and a base. The ointment is for external use in case of disorders of the locomotor apparatus (Author's Certificate 1794454, published on Feb. 15, 1993). However, this composition is not suitable for the care of withering skin.

Known is further a therapeutic and cosmetic balsam representing an extract produced by treating special additives from the group containing hypericum leaves, nettle leaves, milfoil leaves, marigold flowers, fir sesquiterpenes, and pine nut shells, with fir needle oil. This therapeutic and prophylactic balsam has a broad range of pharmacological effects and can be used for increasing the skin tone, elimination of skin irritations, for resolution of hypodermic indurations, for the treatment of arthritis, radiculitis and the like (RU patent 2234935, published on Aug. 27, 2004). In the case of long term application allergic reactions are possible.

Known is, furthermore, a preparation for problematical skin care in the form of a gel containing aqueous extracts of bladder wrack and green tea, aqueous alcoholic extracts of birch leaves, juniper, bottlebrush, and cayenne pepper, and glycerol, Carbopol, triethanolamine, Indian mustard, Nipagin, Nipasol, essential oil of the mandarin, and water. The agent improves the microcirculation, efficiently smoothens and moistens the skin, and has a warming effect (RU patent 2193394, published on Nov. 27, 2002). This preparation can be considered the closest prior art. The preparation is efficient enough in many cases. However, said preparation does not show a prolonged action and has only a slightly rejuvenating effect to the skin.

DISCLOSURE OF THE INVENTION

The object of the present invention is to develop a new efficient therapeutic and cosmetic preparation in the form of an oily balsam.

The object is achieved with a composition of and a method for the manufacture of an oily balsam having a warming, analgesic, anti-inflammatory, and rejuvenating effect, and pleasant organoleptic properties and texture. The achieved technical result is a more prolonged action, and a reduction of term for obtaining a rejuvenating and therapeutic effect.

The oily warming balsam is a homogenous oily system and comprises a complex of oils, emollients, and extracts, namely, Macadamia oil, a dry Boswellia serrata extract (frankincense/olibanum), isopropyl myristate, vegetable oil, an oily extract of red hot pepper, standardized for capsaicin (10 percent), polyethylsiloxane (PES-4), lecithin, and a flavouring agent, with the following ratio of the components (mass percent):

| | |
|---|---|
| *Macadamia* oil | 27.0-33.0 |
| *Boswellia serrate* extract (olibanum) | 15.0-25.0 |
| isopropyl myristate | 8.0-12.0 |
| vegetable oil | 32.35-41.75 |
| oily extract of red hot pepper (10 per cent) | 1.5-2.5 |
| polyethylsiloxane | 0.5-1.0 |
| lecithin | 0.05-0.15 |
| flavouring agent | 0.1-0.2. |

PREFERRED EMBODIMENT OF THE INVENTION

Macadamia is an Australian plant that grows in the north of the state of New South Wales and in the state of Queensland. The oil of the Macadamia is rich of monounsaturated palmitic acid (which is contained in the human skin) that is not present in any other vegetable oil. It perfectly moistens and smoothens the skin and renders it healthy and beautiful. It restores withering, dry skin of face and body.

Since long ago the resin of the holy (insence) tree *Boswellia serrata* that grows in the mountainous regions of India) has been usedas an anti-inflammatory agent for treating arthritis, osteoarthrosis, inflammatory lung and bowel diseases in the traditional Indian medicine "Ajurveda".

The main active agent of this resin are boswellic acids. Studies of extracts of this resin and of the individual boswellic acids showed a significant decrease of anti-inflammatory mediators under the action of said agents. Along with the anti-inflammatory action M. L. Sharma and other authors identified analgesic, antipyretic, immunomodulatory, antibacterial, hepatoprotective, and antihyperlipidemic action of boswellic acids. The dry Boswellia extract can be produced by known methods (e.g., according to WO 0062751).

Pepper has also long since been a well-known plant that has been used in the Indian Ajurvedic medicine for several millenniums. Modern medical studies confirm its immunostimulatory, phagocytic and anti-oxidant properties. The oily extract of the fruit contains piperine, piperolongumin, silvatin, piperolonguminin, philphiline, cytosterol, methyl piperate and a number of piperine-like compounds as well as a complex of vitamins: folic and pantothenic acid, and the vitamins A, B1, B2, B3, B6 and C. The extract of red pepper, having a warming effect on the skin, widens the vessels and activates the local microcirculation. Collectively, these reactions initiate the process of fat splitting, support acceleration of the metabolism in the subcutaneous fat and support a lifting of the skin.

As a vegetable oil preferably refined oils are used, for example, corn oil or sunflower oil.

The oils, which can easily be embedded into the lipid structure of the skin integument, provide an antioxidant protection as they contain natural polyunsaturated fatty acids and the vital lipid soluble vitamins A and E.

A balanced complex of the required active substances is obtained by the use of a complex of oils with extracts of vegetable origin, and the addition of specific emollients, namely, isopropyl myristate and polyethylsiloxane, renders it possible to stabilize the complex and to give it a homogenous structure. The combination of the ingredients gives the preparation also a pleasant smell. And, as is known, in cosmetic science pleasant organoleptic characteristics are of vital practical and commercial importance. The presence of a pleasant smell of the active substances allows for a smaller amount of flavouring agents to be added that nowadays are normally synthetic products. As flavouring agents any of the products that are produced nowadays can be used, e.g., products on the basis of essential oils of rose, fir, jasmine, lemon, camomile, and the like.

The present preparation is suitable for normalizing and restoring the microcirculation of the blood in the skin, for reducing puffiness, relieving fatigue and unpleasant tactual and affective sensations in the skin, for massage in the therapy of radiculitis and various types of muscular strain, as a warming agent in the case of undercooling, but also for the care of withering skin of face and body.

A series of experiments showed that for achieving the object of the invention certain ratios must be observed, i.e., when using several plants, each of which having its specific set of biologically active substances, a synergism of activity is observed, which can not be predicted and could lead, among others, to a potentiation not only of the activity, but also of side effects.

In the physical and chemical characteristics the oily warming balsam shall correspond to the requirements and norms according to Table 1.

TABLE 1

| Characteristics | Norm |
| --- | --- |
| pH value of the aqueous extract, pH | 6.0–7.0 |
| Mass fraction of capsaicin, per cent | 0.15–0.25 |

The formulation of the therapeutical and cosmetic balsam is given in Table 2 in Examples 1-3.

| No. | Ingredient | Normative and technical documentation | Mass fraction, per cent Examples | | |
| --- | --- | --- | --- | --- | --- |
| | | | 1 | 2 | 3 |
| 1 | *Macadamia* oil | imported | 27.0 | 30.0 | 33.0 |
| 2 | *Boswellia serrata* extract (olibanum) | imported | 25.0 | 20.0 | 15.0 |
| 3 | polyethylsiloxane (PES-4) | GOST (Russian Standard) 13004-77 | 1.0 | 1.0 | 0.5 |
| 4 | isopropyl myristate | imported | 12.0 | 10.0 | 8.0 |
| 5 | refined and deodorized corn oil | imported or GOST 8808-73 | 32.35 | 36.75 | 41.75 |
| 6 | oily extract of hot red pepper with 10 percent capsaicid | imported | 2.5 | 2.0 | 1.5 |
| 7 | lecithin (L 45) | imported | 0.05 | 0.05 | 0.15 |
| 8 | flavouring agent | imported | 0.1 | 0.2 | 0.1 |

Example 4

The technological process of producing the oily warming balsam consists in the sequential mixing of the oils and emollients (isopropyl myristate and polyethylsiloxane (PES-4)), dissolution of the plant extract and the lecithin in the mixture at the melting temperature of the highest melting ingredient (lecithin), the ingredients being taken in the formulation ratio, mixing the oil obtained with the oily pepper extract at room temperature, filtration of the desired product, filling and packing.

Method of producing the balsam according to Example 2
a) Preparation of the Oil-Emollient Composition For preparing the oil-emollient composition 30.0 kg of Macadamia oil, 10.0 kg of isopropyl myristate, 1.0 kg of PES-4, and 36.75 kg of corn oil are fed by vacuum to the reactor with a running mixer, and the composition is mixed for 5-10 minutes and heated to a temperature of 60-70° C.
b) Dissolution of the Boswellia Extract Under continuous stirring 20.0 kg of Boswellin (olibanum) extract and 0.05 kg of lecithin are added to the composition of heated oils in small portions until complete dissolution of the components in the oil. Subsequently, the mixture is cooled to room temperature under stirring.
c) Preparation of the Cosmetic Preparation (CP) and Filtration From a service tank 2.0 kg of a 10 percent oily extract of hot pepper and subsequently 0.2 kg of flavouring agent are fed to the reactor containing the mass cooled to room temperature. Then stirring is continued until a homogenous mass is obtained. Air bubbles that formed during the production process are removed by vacuum. Subsequently, the final cosmetic preparation is discharged through a filter.
d) Filling From every lot of the cosmetic preparation a sample is taken for analysis and long-term storage. The guaranteed shelf life of the oily warming balsam is not less than 18 (eighteen) months from the date of production that is indicated on the tube.

Example 5

The formulation comprises allowed components, and was tested according to the requirements of the Sanitary Rules and Norms (SanPIN) 1.2.681-97 "Hygenic requirements for the production and safety of perfumery and cosmetics production", approved on Nov. 20, 1997.

Experimental studies were conducted on female white rats with a body mass of 210 to 220 grams. The results of these studies showed that in case of a single application and also in case of long term application of the balsam to the skin no general toxic, irritating or allergenic effect on the skin of the animals was found: The condition of skin, hair, appetite, behavioral reactions, and weight gain of the tested animals did not differ from that of the control animals. According to the studies on acute toxicity the $LD_{50}$ exceeds 2500 mg/kg, i.e., the product refers to class 4 (little dangerous) according to GOST (Russian National Standard).

Example 6

Clinical studies for measuring the efficacy and tolerability of the oily warming balsam were conducted on 20 volunteers of the age between 40 and 80 years, 19 females and 1 male. The volunteers were kept under observation for 21 days.

All volunteers complained about pain at the joints when moving or when the weather changed. Besides, the volunteers reported a feeling of weight in their legs.

Before the clinical testing the volunteers were subjected to a skin testing of the balsam that was applied to the inner side of the forearm and left on the skin for 24 hours. The results showed no irritating or sensitizing effect of the preparation.

The volunteers used the balsam twice a day. They applied the oily balsam on the skin around the joints till its total absorption. (The balsam was absorbed by the skin within 2-3 minutes.)

Eight volunteers reported a decrease of the pain at the joints when moving after 8-9 days, in ten volunteers the feeling of weight in the legs decreased after 11-12 days of use. All volunteers reported that after 19-20 days of use of the oily balsam the movement of the joints became easier, they felt a feeling of lightness and comfort. Two volunteers did not feel a noticeable improvement of the condition of the joints after use of the balsam. All volunteers did feel a warming effect of the balsam.

The volunteers tolerated the oily warming balsam without any side effects.

Example 7

Evaluation of the Effect on the Skin

Before the start of the study for evaluation of any skin-irritating and sensitizing effect skin tests were conducted on the test persons. There were detected no signs of irritation whatsoever.

On the surface of problem areas of the skin a small amount of balsam was applied, and it was left for absorption for 2-3 minutes. For the control to some areas of the skin a balsam without pepper extract was applied.

For the study a device Skin-scanner (Japan) and an acustic tissue analyzer ASA (Russia) were used. The rate of surface perturbation shifts was registered with the device. The evaluation of the effect of the balsam was conducted by comparing the acoustic properties of the skin before and after a two weeks' use. The positive effect was confirmed by a decrease of the initial rate value in the order of 4 ms. The efficacy was registered by a change of colour and rate of the acoustic wave velocity towards an improvement of the skin characteristics.

In the evaluation a fixing of the elasticity and flexibility of the skin, a disappearance of minor wrinkles, pimples, minor indurations, and an improvement of the colour can be visually observed.

The improvement occurs on average about 20 percent earlier than in case of a control agent, and the effect lasts longer.

INDUSTRIAL APPLICABILITY

The oily balsam is a highly efficient agent for normalization and activation of the microcirculation of the blood in the skin.

The agent has a prolonged warming effect and reduces puffiness and fatigue.

The balsam uses a unique system of transdermal transport that ensures a mild, safe and efficient action of the active components.

For preparing the oily warming balsam raw materials are used that are suitable for the use only in cosmetics, in the pharmaceutical or food industry. Every batch of raw material is subjected to an initial control regarding the basic parameters that characterize its quality.

TABLE 3

| | | | | |
|---|---|---|---|---|
| 1 | *Macadamia* oil | imported | physical form | liquid, transparent |
| 2 | *Boswellia serrata* extract (olibanum) | imported New AMBADI | physical form colour odor | liquid orange-red typical for olibanum |
| 3 | polyethylsiloxane (PES-4) | GOST 13004-77 | physical form | liquid, transparent |
| 4 | isopropyl myristate | imported | physical form | liquid, transparent |
| 5 | refined and deodorized vegetable oil (corn oil) | imported or GOST 8808-73 | physical form colour odor | viscous liquid yellow odorless |
| 6 | oily extract of hot red pepper with 10 per cent capsaicid | imported | physical form colour odor | viscous liquid bright orange-red pepper smell |
| 7 | lecithin | imported | physical form colour odor | wax-like crystals yellowish characteristic |
| 8 | aroma compound | imported | physical form colour odor | oily liquid transparent characteristic |

The agent can be widely used in practise.

The invention claimed is:

1. A therapeutic and cosmetic preparation in the form of an oily balsam, comprising Macadamia oil, olibanum extract from *Boswellia serrata*, isopropyl myristate, vegetable oil, an oily extract of red hot pepper which is standardized to 10% capsaicin, polyethylsiloxane, lecithin and a flavoring agent, wherein the components are present in the following percentages by mass:

| | |
|---|---|
| Macadamia oil | 27.0-33.0 |
| olibanum extract from *Boswellia serrata* | 15.0-25.0 |
| isopropyl myristate | 8.0-12.0 |
| vegetable oil | 32.35-41.75 |
| oily extract of red hot pepper standardized to 10% capsaicin | 1.5-2.5 |
| polyethylsiloxane | 0.5-1.0 |
| lecithin | 0.05-0.15 |
| flavoring agent | 0.1-0.2. |

2. The preparation according to claim 1, wherein the vegetable oil is corn oil.

3. The preparation according to claim 1, which is suitable as a warming agent.

* * * * *